US012714641B2

(12) United States Patent
Altshuler et al.

(10) Patent No.: US 12,714,641 B2
(45) Date of Patent: Aug. 25, 2026

(54) AUTOMATED CARDIAC MASSAGE DEVICE AND METHOD

(71) Applicants: Peter Altshuler, Philadelphia, PA (US); Thais Peres, Philadelphia, PA (US)

(72) Inventors: Peter Altshuler, Philadelphia, PA (US); Thais Peres, Philadelphia, PA (US)

( * ) Notice: Subject to any disclaimer, the term of this patent is extended or adjusted under 35 U.S.C. 154(b) by 841 days.

(21) Appl. No.: 18/091,078

(22) Filed: Dec. 29, 2022

(65) Prior Publication Data

US 2023/0218477 A1 Jul. 13, 2023

Related U.S. Application Data

(60) Provisional application No. 63/294,604, filed on Dec. 29, 2021.

(51) Int. Cl.
*A61H 31/00* (2006.01)
*A61N 1/39* (2006.01)

(52) U.S. Cl.
CPC ......... *A61H 31/005* (2013.01); *A61H 31/006* (2013.01); *A61N 1/39044* (2017.08); *A61H 2201/0107* (2013.01); *A61H 2201/10* (2013.01); *A61H 2201/1676* (2013.01);
(Continued)

(58) Field of Classification Search
CPC .. A61H 31/004; A61H 31/005; A61H 31/006; A61M 60/289; A61M 60/191; A61M 60/839; A61M 60/465; A61M 60/468; A61M 60/50; A61M 60/508;
(Continued)

(56) References Cited

U.S. PATENT DOCUMENTS 4,925,443 A * 5/1990 Heilman ............. A61M 60/538 600/16
6,254,525 B1 * 7/2001 Reinhardt ........... A61M 60/191 623/3.27
(Continued)

FOREIGN PATENT DOCUMENTS

RU 2688722 C1 * 5/2019 ........... A61H 31/008

OTHER PUBLICATIONS

PE2E Translation Uteshev RU_2688722 (Year: 2019).*

*Primary Examiner* — Victoria Murphy
*Assistant Examiner* — Sydney Reyes Russell
(74) *Attorney, Agent, or Firm* — DUBOIS, BRYANT & CAMPBELL, LLP; William D. Wiese

(57) ABSTRACT

An automated cardiac massage device has two dynamic, multilayered compressive units oriented to compress the heart using an outer, non-compliant layer which supports an inner layer made of expandable and compressive material configured to contract and expand to facilitate cardiac filling and ejection. The compressive units are attached to a flexible apex member which modulates the shape and position of the two compressive units to provide maximal apposition to the heart while the device remains in use. Barometric pressure sensors may be incorporated on the inner layer of the compressive unit to measure the systolic and filling diastolic pressure within the heart. A third, detachable, phalange arises from the flexible apex member to provide a third station of support for the heart should the configuration of the compressive units require an additional point of support to secure the heart within the apparatus.

11 Claims, 4 Drawing Sheets

(52) U.S. Cl.
CPC ................ *A61H 2201/5005* (2013.01); *A61H 2201/5043* (2013.01); *A61H 2201/5071* (2013.01)

(58) Field of Classification Search
CPC .......... A61M 60/515; A61N 1/39–3993; A61F 2/2478; A61F 2/2481
See application file for complete search history.

(56) References Cited

U.S. PATENT DOCUMENTS 6,432,039 B1* 8/2002 Wardle .................. A61F 2/2481
600/16
6,464,655 B1* 10/2002 Shahinpoor ......... A61M 60/531
601/153
8,523,756 B2* 9/2013 Lu ....................... A61M 60/289
600/16
8,644,927 B2* 2/2014 Imran ................ A61N 1/36578
607/9
9,538,931 B2* 1/2017 Sullivan ................. A61B 5/361
10,058,647 B2* 8/2018 Roche ................... F15B 15/103
10,987,275 B2* 4/2021 Wijshoff .............. A61B 5/0261
11,052,019 B2* 7/2021 Freeman .............. A61H 31/005
12,109,419 B2* 10/2024 Forsell ................ A61M 60/191
2004/0015041 A1* 1/2004 Melvin ............... A61M 60/191
600/16
2022/0062098 A1* 3/2022 Jamal ................... A61H 31/006
2022/0117838 A1* 4/2022 King .................... A61N 1/3993

* cited by examiner

AUTOMATED CARDIAC MASSAGE DEVICE AND METHOD

PRIORITY STATEMENT UNDER 35 U.S.C. § 119 & 37 C.F.R. § 1.78

This non-provisional application claims priority based upon prior U.S. Provisional Patent Application Ser. No. 63/294,604 filed Dec. 29, 2021 in the names of Peter John Altshuler and Thais Silva Peres entitled "AUTOMATED CARDIAC MASSAGE DEVICE AND METHOD," the disclosures of which are incorporated herein in their entirety by reference as if fully set forth herein.

FIELD OF THE INVENTION

Various embodiments of the present invention include a device configured to be placed around a heart to provide external automated cardiac massage in the setting of cardiac arrest with an open, exposed heart.

BACKGROUND

Trauma resuscitation for patients in extremis in which signs of life have been lost involves the opening of the intrathoracic cavity and delivering the heart to provide open cardiac massage. In this setting, a health care provider traditionally encloses the heart with both hands and compresses the heart repeatedly to maintain perfusion. This technique may also be applied in post-cardiac surgery patients who suffer cardiac arrest post-operatively and have their chest cavity emergently reopened. While open manual cardiac massage is necessary in these settings to maintain perfusion until a sustainable cardiac rhythm is restored, it carries several drawbacks. For example, both massage rate and pressure may vary depending on the provider performing open cardiac massage. In addition, there is a risk of iatrogenic cardiac injury from the massage itself. It also requires the use of a trained clinician, whose complete attention and use of hands must be devoted to the act of open cardiac massage.

Closed cardiopulmonary resuscitation has recently been aided by the use of automated external compression devices to provide reliable, reproducible, high-quality cardiac compression. Its use allows trained clinicians who would otherwise be providing cardiopulmonary resuscitation to be utilized in other critical aspects of patient resuscitation. These devices have been designed for use in closed-chest settings, where the heart remains enclosed within the intrathoracic cavity.

While compression quality and patient outcomes in closed-chest cardiopulmonary resuscitation have been improved with the use of automated compression devices, a need exists for the development of a device and process that similarly provides reliable, reproducible, and controlled automated cardiac massage in the open-chest setting.

BRIEF SUMMARY OF THE INVENTION

Aspects of this invention comprise various configurations of a novel device which seats the apex of the heart securely within a multilayered apparatus and a method for using that apparatus. In various embodiments, two dynamic, multilayered compressive units are oriented to compress the heart using an outer, non-compliant layer which supports an inner layer made of expandable and compressive material configured to contract and expand to facilitate cardiac filling and ejection. These compressive units are attached to, or form an integral part of, a flexible apex member which modulates the shape and position of the two compressive units to provide maximal apposition to the heart while the device remains in use. Barometric pressure sensors may be incorporated on the inner layer of the compressive unit to measure the contraction (systolic) and filling (diastolic) pressure within the heart. These sensors may be transmitted through the device to a digital display on the outside shell of the device which allows for modulation of the inner, compliant layer's contraction and expansion to regulate perfusion pressure during automated massage. A third, detachable, phalange arises from the flexible apex member to provide a third station of support for the heart should the configuration of the compressive units require an additional point of support to secure the heart within the apparatus.

The mechanism by which the inner layer expands and decompresses may be hydraulic, pneumatic, may act through a piston-based internal engine or other compression/decompression methods known in the art. Two compressive units may be oriented 180 degrees from each other, however the malleability of the apex member may allow for adjustment of the orientation of the units to provide for maximal securement and compression dependent upon the clinical scenario.

The inner layer of the compressive unit may contain barometric pressure sensors that come in direct contact and allow for real-time pressure recordings of the pressure exerted back on the machine from the heart itself. This is designed to trigger an alarm when the detected pressure exceeds a set pressure, indicating that the set contractility may be too strong, or that intrinsic cardiac activity may be pushing against the device and capable of providing systemic perfusion.

The inner layer of the compressive unit may contain a stainless steel component which is designed to come in direct contact with the heart. These stainless steel members are connected to an insulated wire which leads to a plug located in the outer layer of one of the compressive units such that it may be connected to commercially available cardioverter defibrillate and used as to defibrillate or cardiovert the heart when clinically indicated.

A support spine which arises as a third phalange off the apex member may also be included to provide further support to the heart. The support spine is comprised of a lightweight, synthetic material, with a base component that allows for easy securement/detachment of the support spine from the apex member. The shape of the support spine may be straight, curvilinear, or a variant thereof that provides for rapid but stable securement on the heart.

The mechanism by which the support spine attaches, or detaches, from the apex member may be through a slotted aperture on the apex member in which a phalange on the support spine may lock into place, or may be comprised of another easily attachable/detachable mechanism should the clinical scenario warrant additional support of the heart beyond the compressive units via the support spine.

Some embodiments include a control unit with a digital display which displays the rate of the compression cycles, the pressure exerted by the device upon the heart, and real-time monitoring of pressure exerted between the heart and the compressive units. Buttons, which may be substituted for dials, allow for the modulation of both compression rate and pressure of compression. An additional button, which may be substituted for a dial, serves to set a pressure in which an alarm will indicate that the compressive force of the device, or the compressive force in addition to the native contractility of the heart, exceeds a certain point. This set-point functions as a means to provide the user of the device with real-time feedback with regards to the pressure the device is exerting on the heart, as well as information as to whether the native heart has intrinsic contractility that may warrant cessation of use of the device. The control unit my also house a socket in which a cardioverter defibrillator may be plugged for use.

The massage device in its entirety, and any variation of the device, is designed to serve as a means to augment cardiac function in an automated fashion in clinical settings in which the heart may be exposed, such as in cases of trauma or post-cardiothoracic surgery, and the native contractility of the heart is insufficient to maintain perfusing pressure to the coronary vessels, pulmonary circulation, cerebral circulation or systemic circulation.

The foregoing has outlined rather broadly certain aspects of a single embodiment of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings. To facilitate these descriptions, like reference numerals designate like structural elements. Embodiments of the disclosure are illustrated by way of example and not by way of limitation in the figures of the accompanying drawings.

DETAILED DESCRIPTION OF THE PREFERRED EMBODIMENTS

Figure 1:
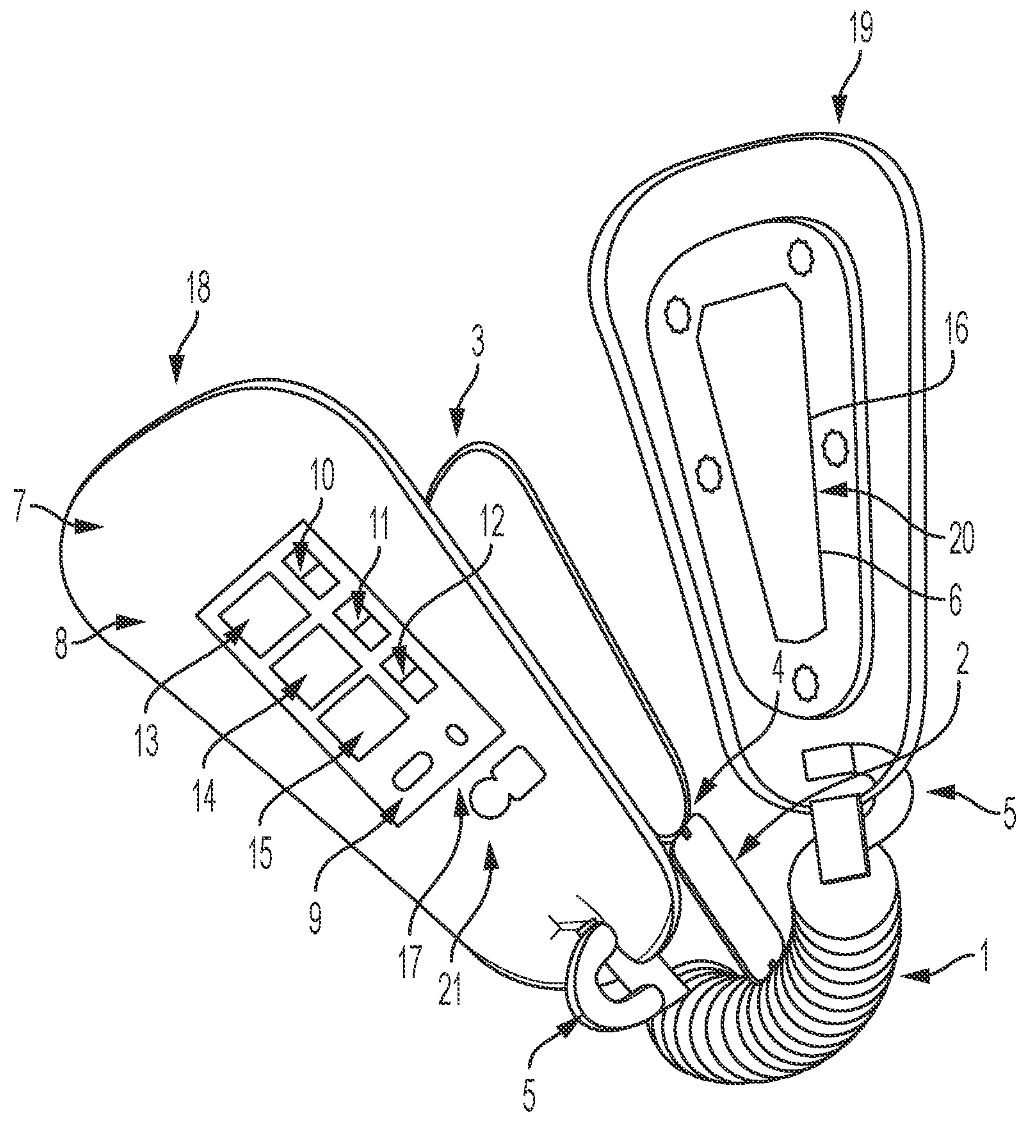
FIG. 1 is a graphical depiction of the entire apparatus, which comprises a malleable apex member, compressive units, barometric pressure sensors, a digital control unit and a third, detachable, phalange.

Described here is a more detailed description of the components and functionality of the automated cardiac massage device and method of using same. The configuration and use of the presently preferred embodiments are discussed in detail below. It should be appreciated, however, that the present invention provides many applicable inventive concepts that can be embodied in a wide variety of contexts other than automated cardiac massage. Accordingly, the specific embodiments discussed are merely illustrative of specific ways to make and use the invention, and do not limit the scope of the invention.

The description may use the phrases "in an embodiment," "in embodiments," "in some embodiments," or "in various embodiments," which may each refer to one or more of the same or different embodiments. Furthermore, the terms "comprising," "including," "having," and the like, as used with respect to embodiments of the present disclosure, are synonymous, and are generally intended as "open" terms (e.g., the term "including" should be interpreted as "including but not limited to," the term "having" should be interpreted as "having at least," the term "includes" should be interpreted as "includes but is not limited to," etc.).

Overview

Turning now descriptively to the drawings, in which similar reference characters denote similar elements throughout the several views, FIGS. 1-4 illustrate the automated cardiac massage device, which comprises a support framework housing two compressive units which serve to compress and relax the heart to support perfusion. The support framework is comprised of a malleable apex member with a support spine that serves to secure the heart in place, allowing for anterior/posterior compression of the heart. The compressive units are modulated by a control unit which allows for modulation of both compression rate, as well as pressure of compressions. An additional barometric pressure sensor on the inside of the compressive units allows for detection of pressure exerted on the heart, as well as pressure exerted back on the device as a means to detect intrinsic cardiac activity, which may be programmed to override the automated massage function if a counter pressure exerted from the heart on the sensor reaches a certain pressure.

Apex Member

Figure 2:
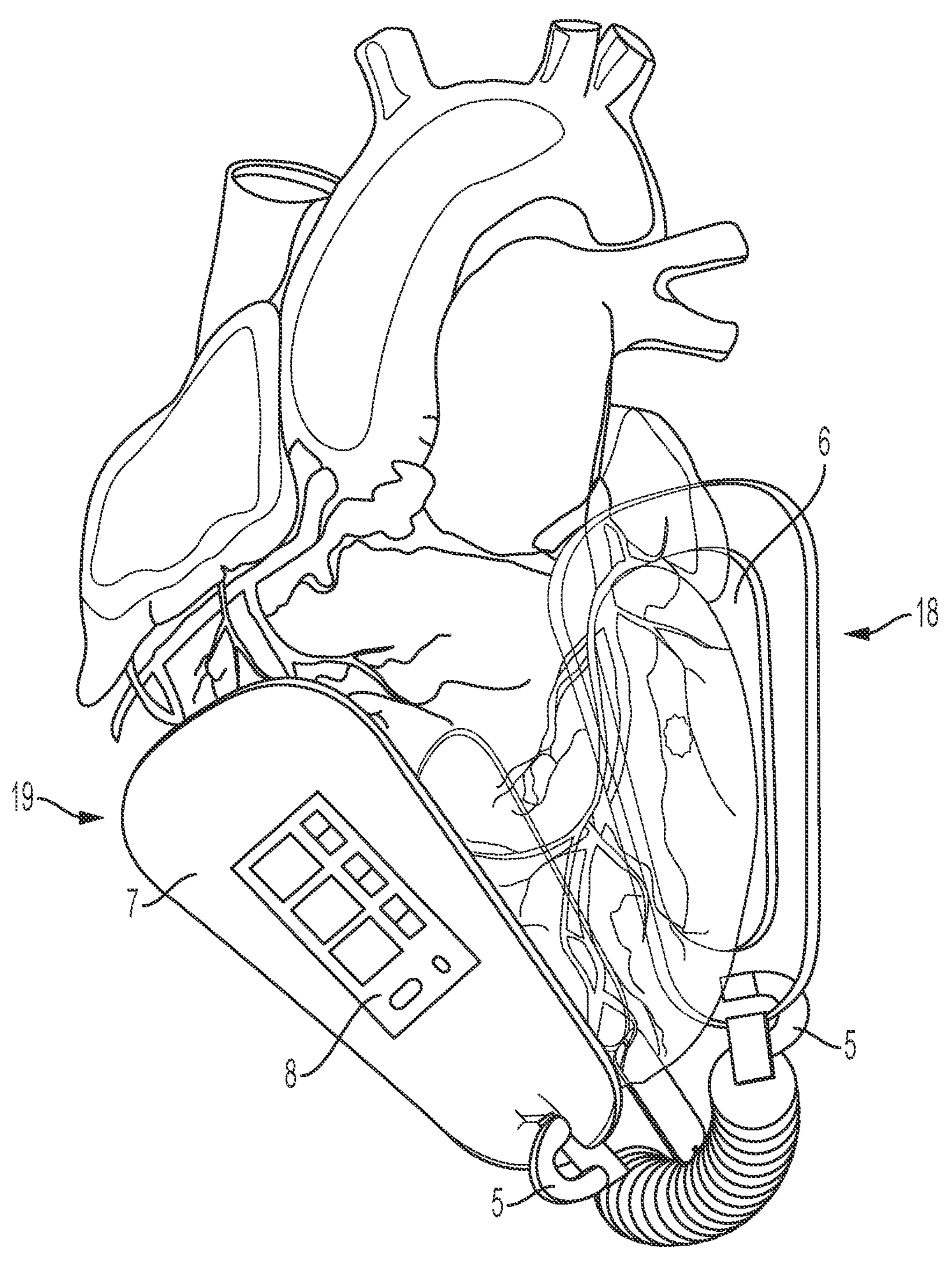
FIG. 2 is a graphical depiction of a heart as it is secured within the entire apparatus.

The apex member 1 of the device is designed to fit over the apex of the heart so that the phalanges may secure the heart in place, as illustrated in FIG. 1, which incorporates the entire device, and FIG. 2, which demonstrates the device as it incorporates a heart into the apparatus. The apex member 1 is preferably comprised of a lightweight, hinged material so as to provide malleability of the apex member 1 to modulate the dimensions of the device to fit securely over any sized heart. In some embodiments, the apex member 1 contains a short spine phalange 2 that can incorporate a detachable support spine 3, which itself is preferably comprised of a lightweight, malleable synthetic material. This support spine 3 may detach from the device at detachment point 4 should the support spine 3 not be necessary to stabilize the compressive units 18 and 19 along the heart.

The apex member 1 is attached to two compressive units 18 and 19 positioned at approximately 180 degrees from each other to provide anterior-posterior compression of the heart, although this may be configured to provide maximal hemodynamic effect should a configuration of something other than 180 degrees provide greater compression. The detachable spine phalange 2 is positioned approximately 90 degrees from each compressive units 18 and 19. However, this also may be modified dependent on the configuration of the two compressive units 18 and 19 to allow for a trimodal support system to encompass the heart.

Compressive Units

Figures 3A, 3B, 3C:
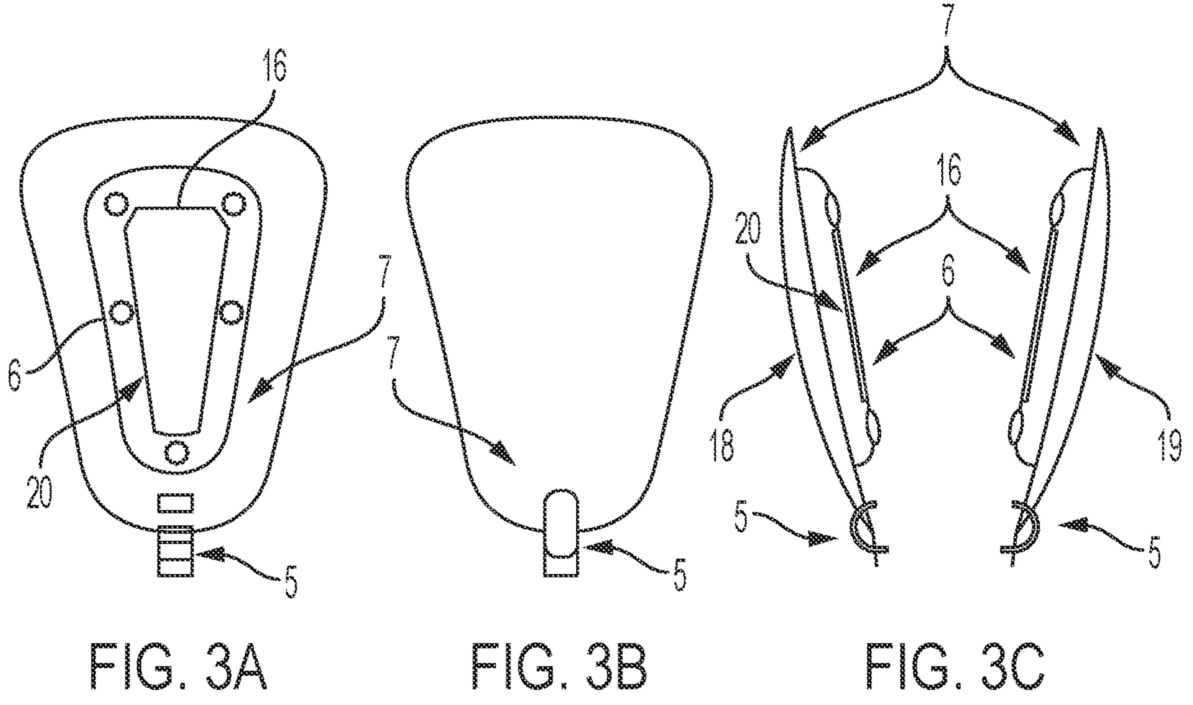
FIG. 3A is a graphical depiction of the anterior-posterior view of one entire compressive unit, that allows for cyclical compression, and relaxation, of the heart during open cardiac massage.
FIG. 3B is a graphical depiction of the posterior-anterior view of one entire compressive unit, that allows for cyclical compression, and relaxation, of the heart during open cardiac massage.
FIG. 3C is a graphical depiction of the lateral projections of one compressive unit, that allows for cyclical compression, and relaxation, of the heart during open cardiac massage.

Embodiments of the compressive units 18 and 19 of the device, shown in FIGS. 1 through 3, utilize two separate layers to provide structure and function to allow for automated cardiac massage. FIG. 3A shows an anterior-posterior view of one entire compressive unit 18 or 19, while FIG. 3B shows a posterior-anterior view and FIG. 3C shows lateral projections of one compressive unit 18 or 19. As it pertains to the entire apparatus, two compressive units 18 and 19 serve to alternate between compression of the heart and passive relaxation and are secured to the apex member 1 via a hinged, locking mechanism 5 so as to allow for the compressive units 18 and 19 to be positioned securely along the heart with the greatest surface area in contact with the heart. This alternating compression and relaxation serve to mimic the intrinsic systolic (compressive) and diastolic (relaxation) function of the heart to allow for perfusion of both coronary vessels as well as systemic and pulmonary circulation.

The structure of each individual compressive units 18 and 19 is demonstrated in FIG. 3, containing both an inner layer 6 and outer layer 7. The outer layer 7 functions as an outer frame, designed as a synthetic, structurally noncompliant frame, and serves to house the inner layer 6 which alternate between compression and relaxation. The outer layer 7 may be composed as a meshed latticework of noncompliant synthetic materials, or may be solid and noncompliant. It is designed as a unit which serves as a frame so that the inner layer 6 sits securely on the heart without exerting hemodynamically significant force inward on the heart when it is secure and in its decompressed state.

Housed within the outer layer 7 is an inner compliant layer 6 that expands and decompresses to allow for repetitive compression and decompression of the heart to facilitate systemic perfusion. The mechanism by which the inner layer 6 expands and decompresses may be hydraulic, pneumatic, may act through a piston-based internal engine or other compression/decompression methods known in the art. This inner layer 6 is to be composed of a synthetic, compliant material, with inherent friction substantial enough to maintain a secure connection with the heart without dislodging from its secured position. The mechanism may be battery powered to allow for cordless function.

In one embodiment, the overall structure of the compressive units 18 and 19 as demonstrated in FIGS. 1 and 2 shows the unit to be trapezoidal and tapered in shape, although in other embodiments the shape may be altered to be triangular such that the base of the triangle corresponds to the base of the heart and apex of the triangle corresponds to the apex of the heart, or rectangular in which the broader end of the unit corresponds to the base of the heart and the narrower end of the unit corresponds to the apex of the heart to better accommodate the conical structure of the heart. The shape of the compressive units 18 and 19 includes those shapes described above but other embodiments may not be limited to those shapes described above. Each compressive unit 18 and 19 is composed of distinct outer and inner subunits.

Support Spine

Figures 4A, 4B:
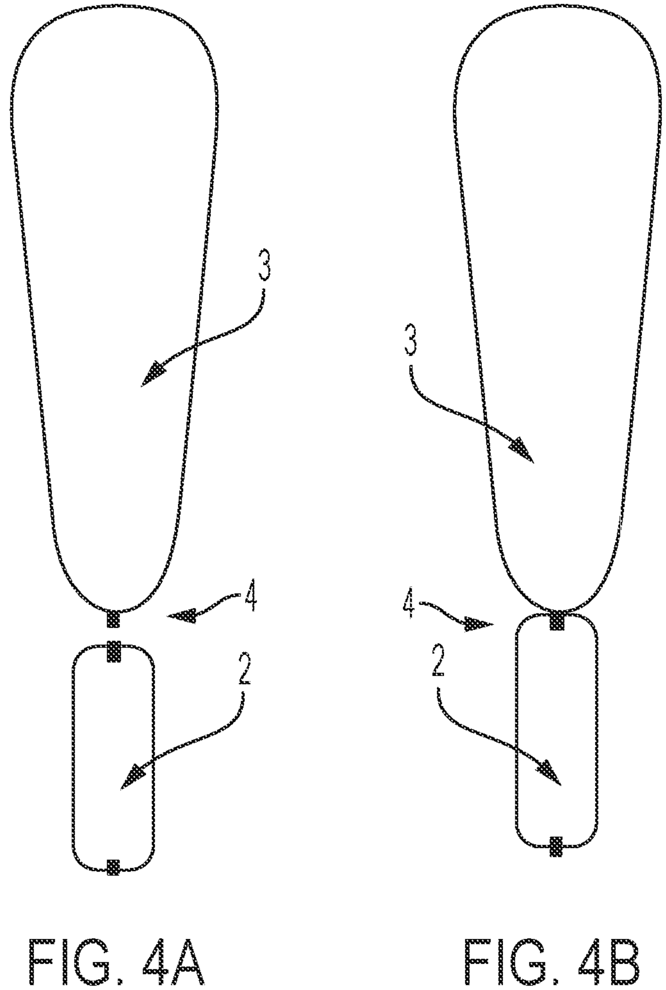
FIG. 4A is a graphical depiction of the detached support spine, which functions as a detachable third phalange arising from the apex member to provide additional structural support to secure the heart within the device.
FIG. 4B is a graphical depiction of the attached support spine, which functions as a detachable third phalange arising from the apex member to provide additional structural support to secure the heart within the device.

In various embodiments of the invention, a support spine 3 serves as a third phalange 2 arising from the apex member 1 to provide further support to the heart. As demonstrated in FIG. 4, this phalange is comprised of a lightweight, synthetic material, with a base component 2 that allows for easy securement/detachment of the support spine 3 from the apex member 1. FIG. 4A demonstrates the individual, detached spine phalange 2 being detached from the support spine 3 at the detachment point 4. In some embodiments, the spine phalange 2 and the support spine 3 are secured together through a locking mechanism located at the detachment point 4. FIG. 4B demonstrates the attached support spine 3. The shape of the support spine 3 may be straight, curvilinear, or a variant thereof that provides for rapid but stable securement on the heart. The mechanism by which the support spine 3 attaches, or detaches, from the apex member 1 may be through a slotted aperture on the apex member 1 in which a phalange on the support spine 3 may lock into place or may be comprised of another easily attachable/detachable mechanism should the clinical scenario warrant additional support of the heart beyond the compressive units 18 and 19 alone.

Control Unit

In various embodiments, the outer surface one of the compressive units 18 and 19 is a control unit 8 which houses an on/off button 9, one or more contraction frequency buttons 10 configured to increase or decrease the frequency of contractions (heart rate), one or more contractile pressure buttons 11 to increase or decrease the contractile pressure, and one or more alarm pressure buttons 12 configured to set a desired alarm pressure. A digital display includes a frequency display 13 and pressure display 14. Additionally, a real-time pressure display 15 displays actual, real-time pressure recordings using the feedback elicited from the barometric pressure sensors 16. These real-time pressure recordings are designed to trigger an alarm 17 when the detected pressure exceeds a set pressure, indicating that the set contractility may be too strong, or that intrinsic cardiac activity may be pushing against the device and capable of providing systemic perfusion. An additional socket 21 may also reside in the control unit so that a cardioverter defibrillator plug, attached to cords leading to a cardioverter defibrillator machine, may be inserted and the device used as a cardioverter defibrillator.

Barometric Pressure Sensors

On the inner surface of one or both of the compressive units 18 and 19, in one or more locations, are barometric pressure sensors 16. These detect the pressure of the heart during contraction and relaxation of the compressive units 18 and 19 and serve several functions. First, the barometric pressure sensor 16 records and modulates the contraction and relaxation pressures the compressive units 18 and 19 exert on the heart. Additionally, the barometric pressure sensor 16 allows for the detection of intrinsic cardiac function as a contractile heart expands and contracts.

By detecting the pressures of both the compressive units 18 and 19 and the heart while each contracts and expands, the barometric pressure sensor can modulate the contractile force, and subsequently systolic and diastolic pressures of the heart to regulate perfusion. This can also serve as a feedback mechanism to alert providers as to the intrinsic heart function, providing information regarding return of spontaneous circulation, and systolic and diastolic pressures of a spontaneously contracting heart. This can be displayed through a real-time pressure display 15 which transmits the data provided by the barometric pressure sensors 16, which may also contain buttons or dials to allow for modulation of the compressive units 18 and 19 with regards to rate and pressure of contraction/expansion. In this fashion, the compressive units 18 and 19 can fully replace the contractility of a non-beating heart, may augment a weakly beating heart, or may stop when the heart contracts and expands at a force and frequency that may support cerebral and systemic perfusion.

Stainless Steel Surfaces for Cardioversion/Defibrillation

In some embodiments, a portion of the inner lining of the inner layer 6 of the compressive units 18 and 19 is a layer of stainless steel 20, attached to an insulated wire (not shown) and connected to the socket 21 adjacent to the control unit 8. This layer of stainless steel 20 can be used to transmit an electrical impulse across the heart when the device is connected to cardio defibrillator machines to allow for cardioversion and/or defibrillation of the heart in the appropriate clinical context.

In Use

In use, the apex member 1 is shaped to the appropriate size such that the spine phalanges 2 can fit securely around the heart in a rapid fashion. The entire apparatus may be secured in place with or without the use of the support spine 3 to function as a third support phalange. The device is secured in place once the compressive units 18 and 19 are secured over the heart such that the entire device remains in place against the heart without causing hemodynamically significant pressure on the heart itself.

Once the compressive units 18 and 19 are secured in place, the on/off button 9 on the control unit 8 may be pushed to engage the device. The desired rate of compressions, the desired pressure the device will exert on the heart, and the pressure at which an alarm will trigger (detected via the barometric pressure sensors 16) can be modulated to the desired settings.

With the device secured against the heart and actively providing cardiac massage, the coronary, pulmonary, and systemic vasculature may be appropriately perfused. This automated cardiac massage device ultimately liberates two hands which would necessarily provide open cardiac massage to continue perfusing the heart, lungs, brain, and body, to provide additional patient care.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for cardiac massage known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

To aid the Patent Office and any readers of any patent issued on this application in interpreting the claims presented in connection with this application, the applicant wishes to note that it does not intend any of the appended claims or claim elements to invoke 35 U.S.C. 112(f) unless the words "means for" or "step for" are explicitly used in the particular claim.

What is claimed:

1. An automated cardiac massage device, comprising:

an apex member configured with two compressive units configured to provide anterior-posterior compression of a heart;

a barometric pressure sensor positioned at an interior portion of at least one of the two compressive units, the barometric pressure sensor configured to provide feedback related to the pressure applied to the heart by the compressive units;

a digital control unit affixed to an exterior portion of at least one compressive unit, the digital control unit configured to control the compression of the compressive units and a support spine configured to secure against the heart and provide further support to the heart; wherein the support spine is configured to be removably attached to the apex member via a spine phalange extending from the apex member by a detachable attachment mechanism.

2. The automated cardiac massage device of claim 1, wherein the detachable attachment mechanism comprises: a slotted aperture or is located at a detachment point.

3. The automated cardiac massage device of claim 1, wherein the apex member is flexible to allow the two compressive units to fit over hearts of different sizes.

4. The automated cardiac massage device of claim 1, wherein the two compressive units are secured to the apex member via a hinged, locking mechanism to allow the compressive units to be positioned securely along the heart.

5. The automated cardiac massage device of claim 1, wherein the two compressive units are comprised of an outer layer that provides a frame for an inner compliant layer that expands and compresses to allow for repetitive compression and decompression of the heart.

6. The automated cardiac massage device of claim 1, wherein the digital control unit provides modulation of both compression rate and compression pressure.

7. The automated cardiac massage device of claim 1, wherein the digital control unit includes a display which displays compression rate and compression pressure to a user.

8. The automated cardiac massage device of claim 1, wherein the digital control unit stops the two compressive units from applying pressure to the heart if the barometric pressure sensors detect pressure exerted on the compressive units by the heart.

9. The automated cardiac massage device of claim 1, wherein the digital control unit is configured to control desired rate of compressions, a desired pressure the two compressive units will exert on the heart, and a pressure at which an alarm will trigger.

10. The automated cardiac massage device of claim 1, wherein the barometric pressure sensor also detects intrinsic cardiac activity that provides counterforce from the heart to at least one of the two compressive units.

11. The automated cardiac massage device of claim 1, wherein the two compressive units are positioned approximately 180 degrees from each other.

* * * * *